United States Patent [19]
Elliott et al.

[11] Patent Number: 6,030,970
[45] Date of Patent: Feb. 29, 2000

[54] ENDOTHELIN RECEPTOR ANTAGONISTS

[75] Inventors: John Duncan Elliott, Wayne; Juan Ignacio Luengo, Audubon; Jia-Ning Xiang, Wayne, all of Pa.

[73] Assignee: Smithkline Beecham Corporation, Philadelphia, Pa.

[21] Appl. No.: 08/750,018

[22] PCT Filed: Aug. 2, 1996

[86] PCT No.: PCT/US96/12584

§ 371 Date: Feb. 2, 1998

§ 102(e) Date: Feb. 2, 1998

[87] PCT Pub. No.: WO97/04774

PCT Pub. Date: Feb. 13, 1997

Related U.S. Application Data

[60] Provisional application No. 60/001,794, Aug. 2, 1995, and provisional application No. 60/011,009, Feb. 1, 1996.

[51] Int. Cl.$^7$ .......................... A61K 31/42; C07D 413/02
[52] U.S. Cl. ........................ 514/236.8; 514/255; 514/256; 514/326; 514/340; 514/342; 514/362; 514/363; 514/364; 514/372; 514/378; 514/380; 544/133; 544/137; 544/333; 544/367; 544/405; 546/209; 546/271.1; 546/272.1; 548/127; 548/128; 548/131; 548/134; 548/136; 548/143; 548/206; 548/213; 548/214; 548/243; 548/247
[58] Field of Search .................. 514/236.8, 255, 514/256, 326, 340, 342, 362, 363, 364, 372, 378, 380; 544/133, 137, 333, 367, 405; 546/209, 271.1, 272.1; 548/127, 128, 131, 134, 136, 143, 206, 213, 214, 243, 247

[56] References Cited

U.S. PATENT DOCUMENTS 3,700,661  10/1972  Saucy et al. ............................ 260/240
4,376,862   3/1983  Junek et al. ............................ 548/249

FOREIGN PATENT DOCUMENTS

WO 95/14863  6/1995  WIPO .
WO 96/07653  3/1996  WIPO .

*Primary Examiner*—Mukund J. Shah
*Assistant Examiner*—Deepak R. Rao
*Attorney, Agent, or Firm*—Linda E. Hall; Stephen A. Venetianer; Charles M. Kinzig

[57] ABSTRACT

Novel to isooxazoles, oxazoles, thiazoles, isothiazoles and imidazoles, pharmaceutical compositions containing these compounds and their use as endothelin receptor antagonists are described.

13 Claims, No Drawings

ENDOTHELIN RECEPTOR ANTAGONISTS

This application is a 371 of PCT/US96/12584 filed Aug. 2, 1996, which claims the benefit of U.S. Provisional Application Ser. No. 60/001,794 filed Aug. 2, 1995 and Ser. No. 60/011,009 filed Feb. 2, 1996

FIELD OF INVENTION

The present invention relates to isooxazoles, oxazoles, thiazoles, isothiazoles and imidazoles, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. *Br. J. Pharm.* 99: 597–601, 1989 and Clozel and Clozel, *Circ. Res.,* 65: 1193–1200, 1989) coronary vasospasm (Fukuda et al., *Eur. J. Pharm.* 165: 301–304, 1989 and Lüscher, *Circ.* 83: 701, 1991) heart failure, proliferation of vascular smooth muscle cells, (Takagi, *Biochem & Biophys. Res. Commun.;* 168: 537–543, 1990, Bobek et al., *Am. J. Physiol.* 258:408-C415, 1990) and atherosclerosis, (Nakaki et al., *Biochem. & Biophys. Res. Commun.* 158: 880–881, 1989, and Lerman et al., *New Eng. J. of Med.* 325: 997–1001, 1991). Increased levels of endothelin have been shown after coronary balloon angioplasty (Kadel et al., No. 2491 *Circ.* 82: 627, 1990).

Further, endothelin has been found to be a potent constrictor of isolated mammalian airway tissue including human bronchus (Uchida et al., *Eur. J. of Pharm.* 154: 227–228 1988, LaGente, *Clin. Exp. Allergy* 20: 343–348, 1990; and Springall et al., *Lancet,* 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle et al., *Br. J. Pharm.* 95: 1011–1013, 1988); Raynaud's phenomenon, Cinniniello et al., *Lancet* 337: 114–115, 1991); Crohn's Disease and ulcerative colitis, Munch et al., *Lancet, Vol.* 339, p. 381; Migraine (Edmeads, Headache, February 1991 p 127); Sepsis (Weitzberg et al., *Circ. Shock* 33: 222–227, 1991; Pittet et al., *Ann. Surg.* 213: 262–264, 1991), Cyclosporin-induced renal failure or hypertension (*Eur. J. Pharmacol.,* 180: 191–192, 1990, *Kidney Int,* 37: 1487–1491, 1990) and endotoxin shock and other endotoxin induced diseases (*Biochem, Biophys. Res. Commun.,* 161: 1220–1227, 1989, *Acta Physiol. Scand.* 137: 317–318, 1989) and inflammatory skin diseases. (*Clin Res.* 41:451 and 484, 1993).

Endothelin has also been implicated in preclampsia of pregnancy. Clark et al. *Am. J. Obstet. Gynecol.* March 1992, p. 962–968; Kamor et al., *N. Eng. J. of Med.,* Nov. 22, 1990, p. 1486–1487; Dekker et al., *Eur J. Ob. and Gyn. and Rep. Bio.* 40 (1991) 215–220; Schiff et al., *Am. J. Ostet. Gynecol.* February 1992, p. 624–628; diabetes mellitus, Takahashi et al., *Diabetologia* (1990) 33:306–310; and acute vascular rejection following kidney transplant, Watschinger et al., *Transplantation* Vol. 52, No. 4, pp. 743–746.

Endothelin stimulates both bone resorption and anabolism and may have a role in the coupling of bone remodeling. Tatrai et al. *Endocrinology,* Vol. 131, p. 603–607.

Endothelin has been reported to stimulate the transport of sperm in the uterine cavity, Casey et al., *J. Clin. Endo and Metabolism,* Vol. 74, No. 1, p. 223–225, therefore endothelin antagonists may be useful as male contraceptives. Endothelin modulates the ovarian/menstrual cycle, Kenegsberg, *J. of Clin. Endo. and Met.,* Vol. 74, No. 1, p. 12, and may also play a role in the regulation of penile vascular tone in man, Lau et al., *Asia Pacific J. of Pharm.,* 1991, 6:287–292 and Tejada et al., *J. Amer. Physio. Soc.* 1991, H1078–H1085. Endothelin also mediates a potent contraction of human prostatic smooth muscle, Langenstroer et al., *J. Urology,* Vol. 149, p. 495–499.

Thus, endothelin receptor antagonists would offer a unique approach toward the pharmacotherapy of hypertension, acute and chronic renal failure, ischemia induced renal failure, sepsis-endotoxin induced renal failure, prophylaxis and/or treatment of radio-contrast induced renal failure, acute and chronic cyclosporin induced renal failure, cerebrovascular disease, cerebrovascular spasm, subarachnoid hemorrhage, myocardial ischemia, angina, congestive heart failure, acute coronary syndrome, myocardial salvage, unstable angina, asthma, primary pulmonary hypertension, pulmonary hypertension secondary to intrinsic pulmonary disease, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, diabetic retinopathy, retinopathy, diabetic nephropathy, diabetic macrovascular disease, atherosclerosis, preclampsia of pregnancy, bone remodeling, kidney transplant, male contraceptives, infertility and priaprism and benign prostatic hypertrophy.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, cerebrovascular vasospasm, myocardial ischemia, angina, congestive heart failure, atherosclerosis, diabetic nephropathy, diabetic retinopathy, retinopathy, diabetic macrovascular disease, atherosclerosis and as an adjunct in angioplasty for prevention of restenosis.

This invention further constitutes a method for antagonizing endothelin receptors in an animal, including humans, which comprises administering to an animal in need thereof an effective amount of a compound of Formula (I).

In a further aspect the present invention provides a process for the preparation of a compound of Formula (I)).

DETAILED DESCRIPTION OF THE INVENTION

The compounds of this invention are represented by structural Formula (I):

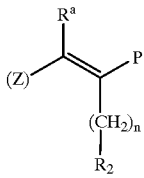
(I)

wherein Z is

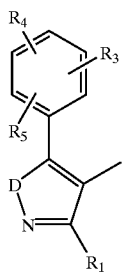
(d)

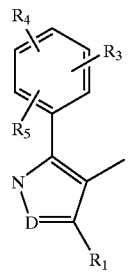
(e)

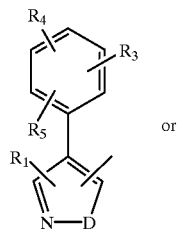
(f)
or

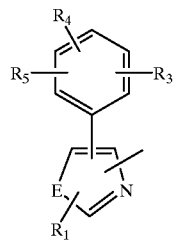
(e)

D is O or S;
E is O, S or $NR_{15}$;
P is tetrazol-5-yl, $CO_2R_6$ or $C(O)N(R_6)S(O)_qR_{10}$;
$R^a$ is independently hydrogen or $C_{1-6}$ alkyl;
$R_1$ is independently hydrogen, Ar, $C_{1-6}$ alkyl or $C_{1-6}$ alkoxy;
$R_2$ is Ar, $C_{1-8}$ alkyl, $C(O)R_{14}$ or

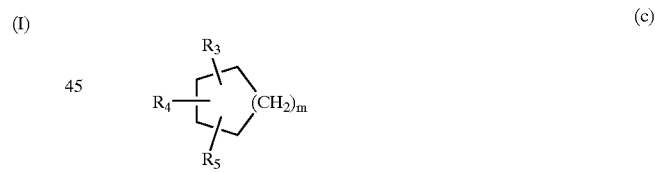
(c)

$R_3$ and $R_5$ are independently $R_{13}OH$, $C_{1-8}$ alkoxy, $S(O)_qR_{11}$, $N(R_6)_2$, $NO_2$, Br, F, I, Cl, $CF_3$, $NHCOR_6$, $R_{13}CO_2R_7$, —X—$R_9$—Y, —X(C($R_6)_2$)$OR_6$, —$(CH_2)_mX'R_8$ or —X$(CH_2)_nR_8$ wherein each methylene group within —X$(CH_2)_nR_8$ may be unsubstituted or substituted by one or two —$(CH_2)_n$Ar groups;
$R_4$ is independently $R_{11}$, OH, $C_{1-5}$ alkoxy, $S(O)_qR_{11}$, $N(R_6)_2$, Br, F, I, Cl or $NHCOR_6$, wherein the $C_{1-5}$ alkoxy may be unsubstituted or substituted by OH, methoxy or halogen;
$R_6$ is independently hydrogen or $C_{1-8}$ alkyl;
$R_7$ is independently hydrogen, $C_{1-10}$ alkyl, $C_{2-10}$ alkenyl or $C_{2-8}$ alkynyl, all of which may be unsubstituted or substituted by one or more OH, $N(R_6)_2$, $CO_2R_{12}$, halogen or $XC_{1-10}$ alkyl; or $R_7$ is $(CH_2)_n$Ar;
$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N$ $(R_6)_2$, $C(R_{11})_2N(R_7)_2$, $C(O)N(R_6)_2$, $NR_7C(O)$ $NR_7SO_2R_{11}$, $OR_6$, or tetrazole which is substituted or unsubstituted by $C_{1-6}$ alkyl;

$R_9$ is independently a bond, $C_{1-10}$ alkylene, $C_{1-10}$ alkenylene, $C_{1-10}$ alkylidene, $C_{1-10}$ alkynylene, all of which may be linear or branched, or phenylene, all of which may be unsubstituted or substituted by one of more OH, $N(R_6)_2$, COOH or halogen;

$R_{10}$ is independently $C_{1-10}$ alkyl, $N(R_6)_2$ or Ar;

$R_{11}$ is independently hydrogen, Ar, $C_{1-8}$ alkyl, $C_{2-8}$ alkenyl, $C_{2-8}$ alkynyl, all of which may be unsubstituted or substituted by one or more OH, $CH_2OH$, $N(R_6)_2$ or halogen;

$R_{12}$ is independently hydrogen, $C_{1-6}$ alkyl, $C_{2-6}$ alkenyl or $C_{2-7}$ alkynyl;

$R_{13}$ is independently divalent Ar, $C_{1-10}$ alkylene, $C_{1-10}$ alkylidene, $C_{2-10}$ alkenylene, all of which may be unsubstituted or substituted by one or more OH, $CH_2OH$, $N(R_6)_2$ or halogen;

$R_{14}$ is independently hydrogen, $C_{1-10}$ alkyl, $XC_{1-10}$ alkyl, Ar or XAr;

$R_{15}$ is independently hydrogen, Ar, $C_{1-6}$ alkyl, or XAr;

$R_{16}$ is independently $C_{1-6}$ alkyl or phenyl substituted by one or more $C_{1-6}$ alkyl, OH, $C_{1-5}$ alkoxy, $S(O)_qR_6$, $N(R_6)_2$, Br, F, I, Cl, $CF_3$ or $NHCOR_6$;

X is independently $(CH_2)_n$, O, $NR_6$ or $S(O)_q$;

X' is independently O, $NR_6$ or $S(O)_q$;

Y is independently $CH_3$ or $X(CH_2)_nAr$;

Ar is:

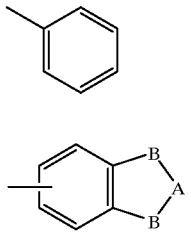

(a)

(b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently (C=O, or $(C(R_6)_2)_m$;

B is independently —$CH_2$— or —O—;

$Z_1$ and $Z_2$ are independently hydrogen, $XR_6$, $C_{1-8}$ alkyl, $(CH_2)_qCO_2R_6$, $C(O)N(R_6)_2$, CN, $(CH_2)_nOH$, $NO_2$, F, Cl, Br, I, $N(R_6)_2$, $NHC(O)R_6$, $O(CH_2)_mC(O)NR_aSO_2R_{16}$, $(CH_2)_mOC(O)NR_aSO_2R_{16}$, $O(CH_2)_mNR_aC(O)$ $NR_aSO_2R_{16}$ or tetrazolyl which may be substituted or unsubstituted by one or two $C_{1-6}$ alkyl, $CF_3$ or $C(O)R_6$;

m is independently 1 to 3;

n is independently 0 to 6;

q is independently 0, 1 or 2;

provided $R_3$, $R_4$ and $R_5$ are not O—$O(CH_2)_nAr$ or O—$OR_6$;

or a pharmaceutically acceptable salt thereof.

All alkyl, alkenyl, alkynyl and alkoxy groups may be straight or branched.

Halogen may be Br, Cl, F or I.

The compounds of the present invention may contain one or more asymmetric carbon atoms and may exist in racemic and optically active form. All of these compounds and diastereoisomers are contemplated to be within the scope of the present invention.

Preferred compounds are those wherein:

P is $CO_2R_6$; more preferably P is $CO_2H$.

$R_1$ is hydrogen.

$R_2$ is Ar, cyclohexyl or $C_{1-4}$ alkyl. More preferably $R_2$ is a group Ar wherein Ar is a group (a) or (b). In said group (a) or (b) $Z_1$ and $Z_2$ are independently hydrogen, $CO_2R_6$, $(CH_2)_nOH$, $C_{1-4}$ alkyl or $C_{1-6}$ alkoxy, e.g. methoxy; A is preferably $CH_2$, and one or both Bs are preferably O.

$R_3$ and $R_5$ are independently hydrogen, $CO_2R_6$, OH, $C_{1-8}$ alkoxy, $C_{1-8}$ alkyl, $N(R_6)_2$, $NO_2$, Br, F, Cl, I, $R_{13}CO_2R_7$, $X(CH_2)_nR_8$, $(CH_2)_mX'R_8$, or $X(C(R_6)_2)_mOR_6$;

In the context of the group $R_3$ and $R_5$ preferably do not represent hydrogen. In particular in the group $R_3$ preferably represents Br, Cl, $C_{1-8}$ alkoxy e.g. methoxy; $X(CH_2)_nR_8$, wherein X preferably represents O, n is 0, 1, or 2, and $R_8$ is preferably selected from:

$CO_2R_6$ wherein $R_6$ is preferably hydrogen;

$OR_6$ wherein $R_6$ is preferably H;

tetrazolyl optionally substituted by $C_{1-8}$ alkyl e.g. ethyl;

$CONR_7SO_2R_{11}$ wherein $R_7$ is H or $C_{1-8}$ alkyl e.g. methyl, $R_{11}$ preferably is $C_{1-8}$ alkyl (e.g. methyl, isopryl, or t-butyl) or phenyl optionally substituted by Br, Cl, F, $C_{18}$ alkyl e.g. methyl;

or $R_8$ is phenyl or pyridyl substituted by one or more Br, Cl, $CO_2H$, $CH_2OH$.

$R_5$ is $C_{1-8}$ alkoxy e.g. methoxy, or $N(R_6)_2$ wherein $R_6$ preferably is H or methyl.

$R_4$ is hydrogen, OH, $C_{1-5}$ alkoxy, $N(R_6)_2$, Br, F, Cl, I, $NHCOCH_3$, or $S(O)_qC_{1-5}$ alkyl wherein the $C_{1-5}$ alkyl may be unsubstituted or substituted by OH, methoxy or halogen. $R_4$ is more preferably hydrogen;

$R_6$ is hydrogen or $C_{1-8}$ alkyl e.g. methyl and ethyl;

$R_7$ is hydrogen, $C_{1-10}$ alkyl, $C_{2-10}$ alkenyl or $C_{2-8}$ alkynyl, all of which may be unsubstituted or substituted by one or more OH, $N(R_6)_2$, $CO_2R_{12}$, halogen, or $R_7$ is $(CH_2)_nAr$. When $R_7$ is $(CH_2)_nAr$, n is preferably zero or 1 and Ar is preferably phenyl substituted or unsubstituted by halogen or $C_{1-5}$ alkoxy.

$R_{11}$ is hydrogen, phenyl, pyridyl wherein the phenyl and pyridyl may be substituted or unsubstituted by one or two $C_{1-4}$ alkyl groups; $C_{1-8}$ alkyl, $C_{2-8}$ alkenyl, $C_{2-8}$ alkynyl, all of which may be substituted or unsubstituted by one or more OH, $CH_2OH$, $N(R_6)_2$, or halogen;

$R_{12}$ is hydrogen or $C_{1-6}$ alkyl.

$R_{13}$ is phenyl, pyridyl, or $C_{2-10}$ alkylene, all of which may be unsubstituted or substituted by one or more $CO_2R_6$, OH, $CH_2OH$, $N(R_6)_2$, or halogen;

$R_{15}$ is preferably hydrogen or $C_{1-6}$ alkyl e.g. ethyl, isopropyl, n-butyl, cyclopropylmethyl or cyclopropylethyl.

The preferred compounds are:

(E)-3-[1-n-Butyl-5-[2-(2-carboxyphenyl)methoxy-4-methoxyphenyl]-1H-imidazol-4-yl]-2-[(2-methoxy-4,5-methylenedioxy)phenylmethyl]-prop-2-enoic acid;

(E)-alpha-[[5-[2-[(2-carboxyphenyl)methoxy]-4-methoxyphenyl]isoxazol-4-yl]methylene]-6-methoxy-1,3-benzodioxole-5-propanoic acid;

(E)-alpha-[[3-[2-[(2-carboxyphenyl)methoxy]-4-methoxyphenyl]isoxazol-4-yl]methylene]-6-methoxy-1,3-benzodioxole-5-propanoic acid; and (E)-alpha-[[3-Butyl-4-[2-[(2-carboxyphenyl)methoxy]-4-methoxyphenyl]isoxazol-5-yl]methylene]-6-methoxy-1,3-benzodioxole-5-propanoic acid.

Compounds of the Formula (Ie),

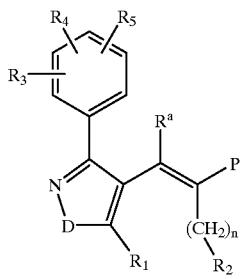
(Ie)

in which $R^a$ is H and D is O, can be prepared by Knoevenagel condensation of a 3-formyl chromone of Formula (2)

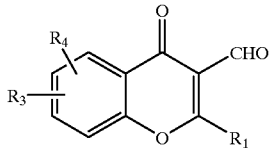
(2)

with a half acid of Formula (3), wherein $R_{16}$ is allyl

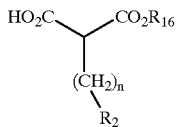
(3)

in a solvent such as benzene at reflux, in the presence of piperidinium acetate with azeotropic removal of water using a Dean-Stark apparatus to afford an ester of Formula (4).

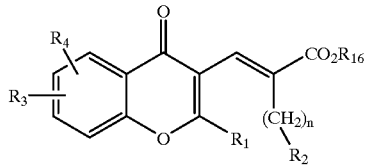
(4)

Compounds of Formula (2) are commercially available or may be prepared by treatment of a phenol of Formula (5)

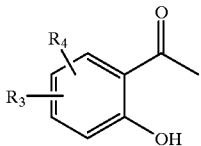
(5)

with boron trifluoride etherate in acetic anhydride followed by treatment with Vilsmeier reagent in dimethyl formamide according to the procedure of Hogberg et al. (*Acta Chem. Scand.* 1984, B38, 359–366)

Reaction of compound (4) with hydroxylamine hydrochloride ($NH_2OH.HCl$) in a suitable solvent such as aqueous ethanol at reflux and in the presence of a base such as sodium acetate provides a phenol of Formula (6).

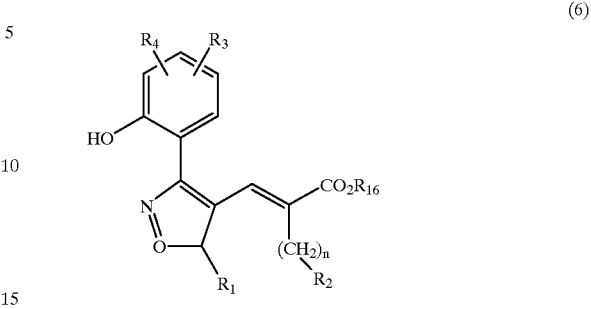
(6)

Alkylation of a phenol of Formula (6) using a bromide of Formula (7), wherein $R_{16}$ is allyl

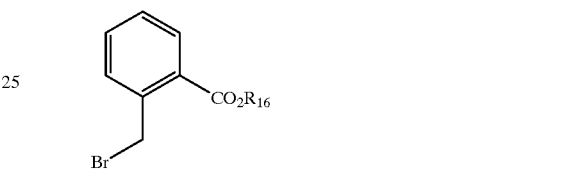
(7)

in the presence of a base such as sodium hydride in a solvent such as dimethylformamide affords a compound of Formula (8).

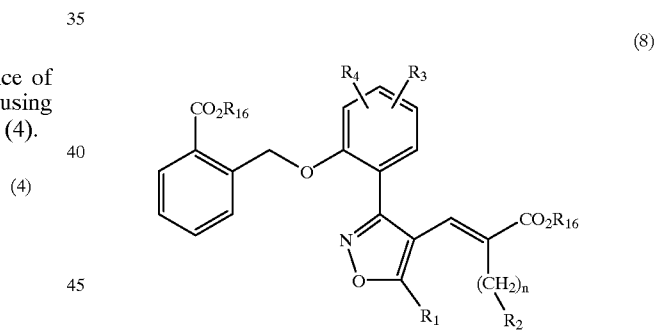
(8)

Deprotection of diallyl ester of Formula (8) using triethylsilane in the presence of a catalytic amount of tetrakis(triphenylphosphine)palladium(0) in a suitable solvent such as tetrahydrofuran at reflux affords, after acidification with acetic acid, an acid of the Formula (Ie), wherein $R^a$ is H, P is $CO_2H$ and D is O.

Alternatively, compounds of Formula (Ie) can be prepared starting from the reaction of a keto ester of Formula (9), wherein $R_{16}$ is allyl

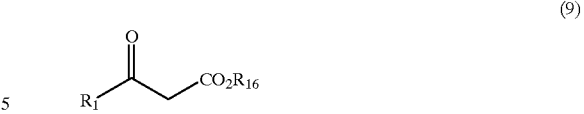
(9)

with an acyl chloride of Formula (10)

(10)

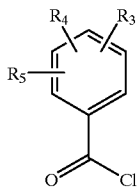

in the presence of a base such as sodium in a solvent such as benzene, to provide a compound of Formula (12)

(12)

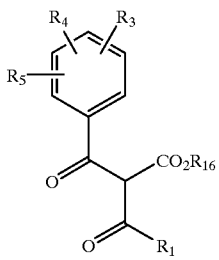

Compound of Formula (12) can be treated with hydroxylamine hydrochloride ($NH_2OH \cdot HCl$) in a suitable solvent such as pyridine at reflux, to provide an isoxazole of Formula (13).

(13)

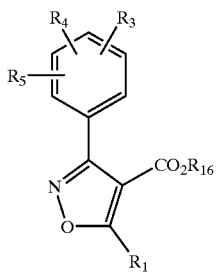

Conversion of an allyl ester of Formula (13) using triethylsilane in the presence of a catalytic amount of tetrakis(triphenylphosphine)palladium(0) in a suitable solvent such as tetrahydrofuran at reflux affords, after acidification with acetic acid an acid of the Formula (14).

(14)

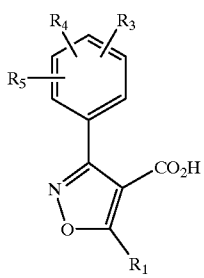

Compound of Formula (14) can be converted to the corresponding N-methyl-O-methylcarboxamide of Formula (15)

(15)

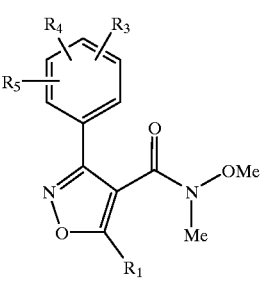

upon treatment with methyl choroformate followed by N,O-dimethylhydroxylaine hydrochloride in the presence of a base such as N-methylpiperidine. Compound of Formula (15) can be treated with an organometallic reagent of Formula (16)

$$R^a\text{-M} \quad (16)$$

wherein $R^a$ is $C_{1-6}$ alkyl and M is either Li or MgCl, following the procedure of Nahm and Weinreb (Tetrahedron Lett. 1981, 39, 3815), to provide a compound of Formula (17), wherein $R^a$ is $C_{1-6}$ alkyl.

(17)

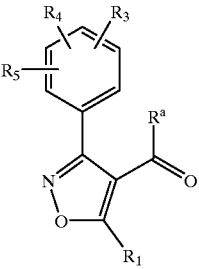

Alternatively, a compound of Formula (17), wherein $R^a$ is H, can be obtained by treatment of carboxamide of Formula (15) with lithium aluminum hydride in a solvent such as anhydrous ether.

Reaction of compound of Formula (17) with the the lithium enolate of an ester of Formula (18), wherein $R_{16}$ is allyl (18)

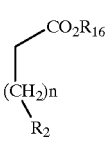

generated by by treatment of (18) with lithium diisopropylamide at −78° C. under an inert atmosphere in a solvent such as tetrahydrofuran, provides an alcohol of Formula (19)

(19)

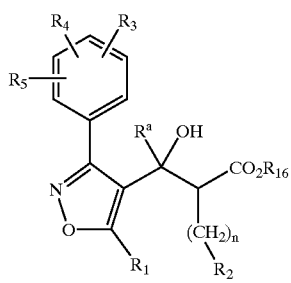

Dehydration of compound of Formula (19) with acetic anhydride followed by treatment with a base such as 1,8-diazabicyclo[5.4.0]undec-7-ene provides a compound of Formula (20)

(20)

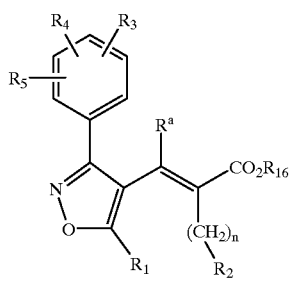

Alternatively, reaction of compound (17), wherein $R^a$ is $C_{1-6}$ alkyl, with Lawesson's reagent [2,4-bis(4-methoxyphenyl)-1,3-dithia-2,4-diphosphetane-2,4-disulfide] in a suitable solvent such as tetrahydrofuran affords a thione of Formula (21).

(21)

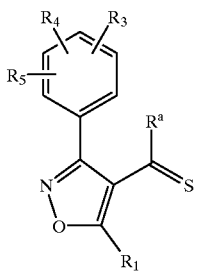

Reaction of a compound of Formula (21) with a diazoester of Formula (22), wherein $R_{16}$ is allyl (22)

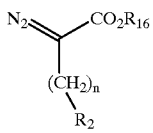

in refluxing tetrahydrofuran affords thiirane (23).

(23)

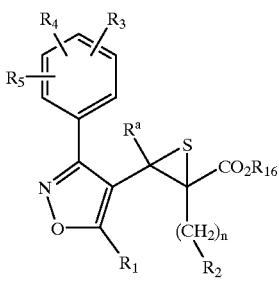

A diazoester of Formula (22) can be prepared from the corresponding ester (18) by treatment with lithium diisopropylamide at −78° C. in a solvent such as anhydrous tetrahydrofuran, followed by the addition of ethyl formate to produce a formylated ester of structure (24).

(24)

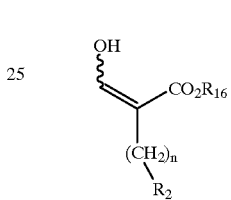

Compounds of Formula (24) can be treated with an arylsulfonylazide such as 4-carboxyphenylsulfonyl azide in the presence of a base such as triethylamine followed by treatment with a base such as aqueous potassium hydroxide to afford diazoesters of type (22).

Treatment of a thiirane of Formula (23) with trimethylphosphite at reflux in a solvent such as chloroform provides compounds of Formula (20), wherein $R^a$ is $C_{1-6}$ alkyl.

Deprotection of allyl ester of Formula (20) using triethylsilane in the presence of a catalytic amount of tetrakis(triphenylphosphine)palladium(0) in a suitable solvent such as tetrahydrofuran at reflux affords, after acidification with acetic acid, an acid of the Formula (Ie), wherein P is $CO_2H$ and D is O.

(Id)

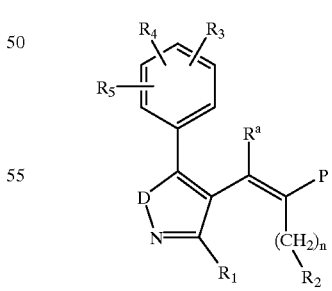

Compounds of Formula (Id), wherein D is O, can be prepared starting from compound (12) by treatment with hydroxylamine hydrochloride ($NH_2OH.HCl$) in a suitable solvent such as methanol, following the procedure of Nair and Wadodkar, Indian J. Chem., Sect B, 1982, 21, 573, to provide an isoxazole of Formula (25).

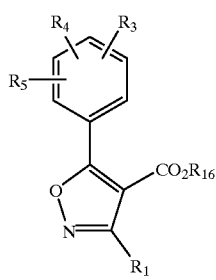
(25)

Compound of Formula (25) can be subsequently converted to compounds of Formula (Id) following the same synthetic scheme as the one described above for the conversion of compound (13) to compound (Ie).

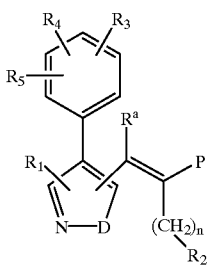
(If)

Compounds of Formula (If) can be prepared starting by commercially available ketones of Formula (26)

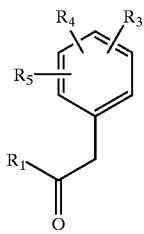
(26)

by reaction with diallyl oxalate of Formula (27)

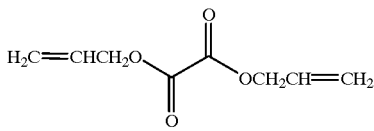
(27)

in the presence of a base such as sodium in a solvent such as allyl alcohol to produce a diketone of Formula (28), ), wherein $R_{16}$ is allyl.

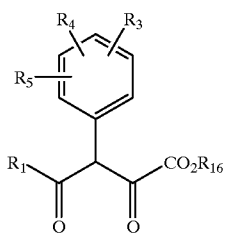
(28)

Reaction of a diketone of Formula (28) with hydroxylamine hydrochloride ($NH_2OH \cdot HCl$) in a suitable solvent such as pyridine at reflux provides an isoxazole of Formula (29).

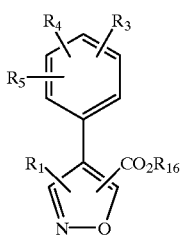
(29)

Deprotection of allyl ester of Formula (29) using triethylsilane in the presence of a catalytic amount of tetrakis (triphenylphosphine)palladium(0) in a suitable solvent such as tetrahydrofuran at reflux affords, after acidification with acetic acid, an acid of the Formula (30),

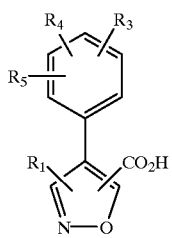
(30)

which can be subsequently converted to the corresponding N-methoxy-N-methylamide of Formula (31)

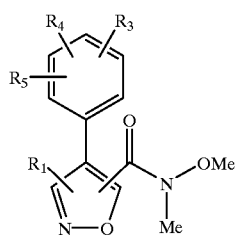
(31)

by treatment with methyl choroformate followed by N,O-dimethylhydroxylamine hydrochloride in the presence of a base such as N-methylpiperidine. Compound of Formula (31) can be treated with an organometallic reagent of Formula (16) to provide a compound of Formula (32), wherein $R^a$ is $C_{1-6}$ alkyl.

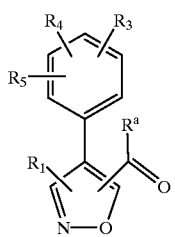
(32)

Alternatively, compound (31) can be treated with with lithium aluminum hydride in a solvent such as diethyl ether to provide a compound of Formula (32), wherein $R^a$ is H. Reaction of compound of Formula (32) with the the lithium enolate of an ester of Formula (18) provides an alcohol of Formula (33)

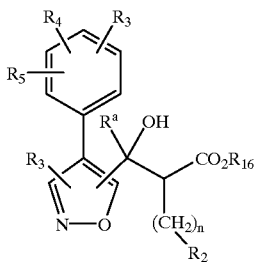
(33)

Dehydration of compound of Formula (33) with acetic anhydride followed by treatment with a base such as 1,8-diazabicyclo[5.4.0]undec-7-ene provides a compound of Formula (34)

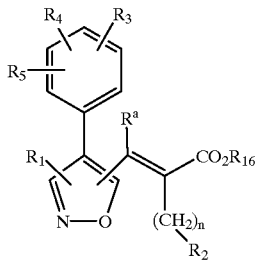
(34)

Alternatively, reaction of compound (32), wherein $R^a$ is $C_{1-6}$ alkyl, with Lawesson's reagent in a suitable solvent such as tetrahydrofuran affords a thione of Formula (35),

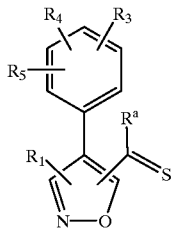
(35)

which can be treated with diazoester (22) in refluxing tetrahydrofuran to provide a thiirane of Formula (36).

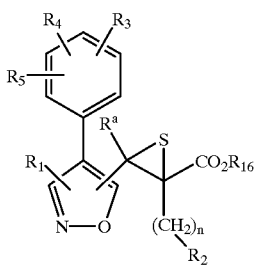
(36)

Treatment of a thiirane of Formula (36) with trimethylphosphite at reflux in a solvent such as chloroform provides compounds of Formula (34), wherein $R^a$ is $C_{1-6}$ alkyl.

Deprotection of allyl ester of Formula (34) using triethylsilane in the presence of a catalytic amount of tetrakis(triphenylphosphine)palladium(0) in a suitable solvent such as tetrahydrofuran at reflux affords, after acidification with acetic acid, an acid of the Formula (Ii), wherein P is $CO_2H$ and D is O.

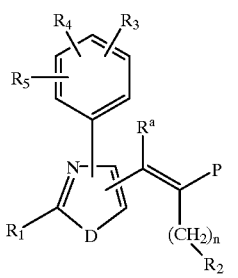
(Ig)

Compounds of Formula (Ig) can be prepared by a process which comprises treating an aryl halide of Formula (37), where Z is I, Br, or Cl

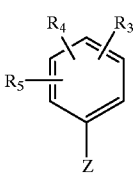
(37)

with an appropriate alkyllithium reagent such as n-butyllithium in tetrahydrofuran by addition of a borate such as triisopropyl borate and acidic work up affords a boronic acid of Formula (38)

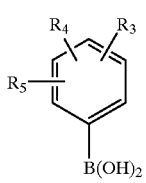
(38)

Reaction of a boronic acid of Formula (38) with a compound of Formula (39)

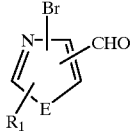
(39)

in the presence of a suitable base such as potassium carbonate with a palladium catalyst such as tetrakis(triphenylphosphine)palladium(0) in a mixture of toluene, ethanol and water at approximately 80–100° C. provides a compound of Formula of (40)

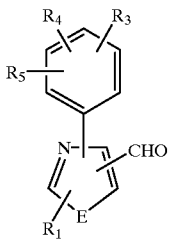
(40)

Knoevenagel condensation of an aldehyde of Formula (40) with a half acid of Formula (3), wherein $R_{16}$ is $C_{1-8}$ alkyl, in a solvent such as benzene ar reflux, in the presence of piperidinium acetate with azeotropic removal of water using a Dean-Stark apparatus, affords an ester of Formula (41)

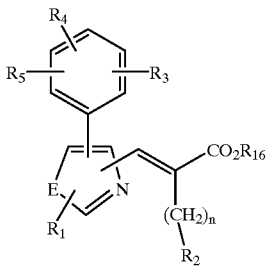
(41)

Saponification of an ester of Formula (41) using aqueous sodium hydroxide in a solvent such as ethanol provides, after acidification with aqueous hydrochloric acid, an acid of Formula (Ig), wherein $R^a$ is H and P is $CO_2H$.

The invention also is a process for preparing compounds of Formula (I) by:

(a) Reaction of a compound of Formula (II)

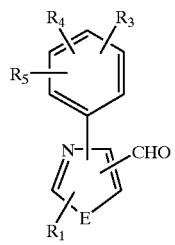
(II)

or a protected form or precursor thereof (as defined hereinafter) with a compound of Formula (3)

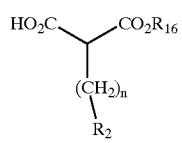
(3)

(wherein $R_2$ and $R_{16}$ are as defined for Formula (I) hereinabove); followed if necessary or desired by:
(b) conversion of one compound of Formula (I) into a different compound of Formula (I) e.g.
  (i) when Formula (I) contains a group $CO_2R_6$, $CO_2R_7$ or $CO_2R_{12}$ wherein $R_6$, $R_7$ or $R_{12}$ is alkyl, conversion to a corresponding compound where $R_6$, $R_7$ or $R_{12}$ represents hydrogen;
  (ii) when Formula (I) contains a hydroxy group (e.g. in $R_3$, $R_4$ or $R_5$) conversion to a different group, e.g. a group $(CH_2)Ar$ where Ar is optionally substituted phenyl, by method well known in the art; and/or
(c) salt formation.

It will be appreciated by those skilled in the art that the substitutents $R_3$, $R_4$, $R_5$, $R_{15}$ and $Z_1$ and $Z_2$ may be introduced at any appropriate stage of the synthesis, preferably at an early stage, using methods well known in the art. In some of the reactions depicted above, particularly those in the early stages of the overall synthesis, one or more of the substitutents may therefore represent a precursor for the eventual substituent. A precursor for any of the substitutents means a group which may be derivatised or converted into the desired group. It will be further appreciated that it may be necessary or desirable to protect certain of these substitutents(or their precursors) at various stages in the reaction sequence. Suitable precursors and protecting groups are well known to those skilled in the art, as are methods for their conversion or removal respectively.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) CHO cell membrane preparation.

CHO cells stably transfected with human ETA and ETB receptors were grown in 245 mm×245 mm tissue culture plates in Dulbecco's modified Eagle's medium supplemented with 10% fetal bovine serum. The confluent cells were washed with Dulbecco's phosphate-buffered saline containing a protease inhibitor cocktail (5 rrm EDTA, 0.5 mM PMSF, 5 ug/ml of leupeptin and 0.1 U/mil of aprotinin) and scraped in the same buffer. After centrifugation at 800× g, the cells were lysed by freezing in liquid nitrogen and thawing on ice followed by homogenization (30 times using a glass dounce homogenizer) in lysis buffer containing 20 mM Tris HCI, pH 7.5, and the protease inhibitor cocktail. After an initial centrifugation at 800× g for 10 min to remove unbroken cells and nuclei, the supernatants were centrifuged at 40,000× g for 15 min and the pellet was resuspended in 50 mM Tris HCI, pH 7.5, and 10 mM $MgCl_2$ and stored in small aliquots at −70° C. after freezing in liquid $N_2$. Protein was determined by using the BCA method and BSA as the standard.

(B) Binding studies.

[$^{125}$I]ET-1 binding to membranes prepared from CHO cells was performed following the procedure of Elshourbagy et al. (1993). Briefly, the assay was initiated in a 100 ul volume by adding 25 ul of [$^{125}$I]ET-1 (0.2–0.3 nM) in 0.05% BSA to membranes in the absence (total binding) or presence (nonspecific binding) of 100 nM unlabeled ET-1. The concentrations of membrane proteins were 0.5 and 0.05 ug per assay tube for ETA and ETB receptors, respectively. The incubations (30° C., 60 min) were stopped by dilution with cold buffer (20 mM Tris HCI, pH 7.6, and 10 mM $MgCl_2$) and filtering through Whatman GF/C filters (Clifton, N.J.) presoaked in 0.1% BSA. The filters were washed 3 times (5 ml each time) with the same buffer by using a Brandel cell harvester and were counted by using a gamma counter at 75% efficiency.

The following examples are illustrative and are not limiting of the compounds of this invention.

EXAMPLE 1

(E)-Ethyl alpha-[[3-[4-methoxy-2-[[2-(methoxycarbonyl)phenyl]methoxy]-phenyl] isoxazol-4-yl]methylene]-6-methoxy-1,3-benzodioxole-5-propanoate a) (E)-Ethyl 6-Methoxy-alpha-[(7-methoxy-4-oxo-4H-1-benzopyran-3-yl)methylene]-1,3-benzodioxole-5-propanoate A solution of 3-formyl-7-methoxychromone (0.67 g, 3.3 mmol) and ethyl hydrogen 2-[(6-methoxy-3,4-methylenedioxy)benzyl]malonate (0.89 g, 3.0 mmol) in benzene (30 mL) was treated with piperidine (0.15 mL, 1.5 mmol) followed by acetic acid (0.085 mL, 1.5 mmol). The reaction was stirred at reflux equipped with a Dean Stark apparatus for 2 h. The mixture was cooled then extracted with EtOAc (200 mL). The organic extract was washed successively with saturated $NaHCO_3$ and brine, dried ($MgSO_4$) and concentrated under vacuum. The resulting residue was purified by column chromatography (silica gel, EtOAc/hexane, gradient 75:25 to 70:30) to afford a material consisting of a 1.2:1 mixture of E:Z enoates as an oil (1.02 g, 78%). Recrystallization of this material from ethanol affords the title compound as the E-isomer, exclusively. Data for the E-isomer: mp 140–141° C.; MS (ESI) t/z 439 (M+H)$^+$. Anal. Calcd for $C_{24}H_{22}O_8$: C, 65.75; H, 5.06. Found: C, 65.56; H, 4.99.

b) (E)-Ethyl (E)-alpha-[[3-(2-hydroxy-4-methoxyphenyl) isoxazol-4-yl]methylene]-6-methoxy-1,3-benzodioxole-5-propanoate A solution of the compound of Example 1 (a) (0.701 g, 1.6 mmol of a 1:1 E:Z mixture), hydroxylamine hydrochloride (0.222 g, 3.2 mmol) and sodium acetate trihydrate (0.870 g, 6.4 mmol) in a mixture of 9:1 EtOH:H$_2$O(32 mL) was stirred at reflux for 1 h. The reaction mixture was cooled and subsequently partitioned between EtOAc (150 mL) and aqueous pH 7 buffer. The organic extract was washed with brine, dried (Na$_2$SO$_4$) and concentrated under vacuum. The resulting residue was purified by column chromatography (silica gel, CH$_2$Cl$_2$/hexane/EtOAc, 90:5:5 to 80:10:10) to afford the title compound (245 mg, 34%), that crystallized upon standing. mp 122–123.5° C. MS (ESI) m/z 454 (M+H)$^+$.

c) (E)-Ethyl alpha-[[3-[4-methoxy-2-[[2-(methoxycarbonyl)phenyl]methoxy]-phenyl]isoxazol-4-yl]methylene]-6-methoxy-1,3-benzodioxole-5-propanoate A solution of the compound of Example 1(b) (0.252 g, 0.58 mmol) in DMF (1.5 mL) was added dropwise to a slurry of NaH (0.022 g, 0.93 mmol) in DMF (1.4 mL) at room temperature. The reaction was stirred for 3 min at which time was added methyl 2-(bromomethyl)benzoate (0.21 g, 0.93 mmol) and stirring continued for 1 h at room temperature. The mixture was quenched with aqueous pH 7 buffer, then diluted with EtOAc. The organic extract was washed with brine, dried (Na$_2$SO$_4$) and concentrated under vacuum. The resulting residue was purified by column chromatography (silica gel, 75:25 hexane/EtOAc) to afford the title compound (84.5 mg, 24%) as a white solid. mp 135–137° C. MS (ESI) m/z 602 (M+H)$^+$.

EXAMPLE 2

(E)-3-[1-n-Butyl-5-[2-(2-carboxyphenyl)methoxy-4-methoxyphenyl]-1H-imidazol-4-yl]-2-[(2-methoxy-4,5-methylenedioxy)phenylmethyl]-2-propenoic acid a) Ethyl 2-amino-2-cyanoacetate To aluminum foil (25 g) was added a solution of mercury (II) chloride (10 g, 0.37 mol) in water (1 L). The mixture was swirled for 5 min, and then the turbid solution was decanted off. The resulting aluminum amalgam was washed successively with water, methanol and diethyl ether. To amalgam suspended in diethyl ether (500 mL) at 0° C., was added a solution of ethyl 2-hydroxyimino-2-cyanoacetate (100 g, 0.70 mol) in diethyl ether (300 mL), followed by water (50 mnL), maintaining a gentle reflux. After 1 h of stirring, the mixture was filtered and the filtrate was washed with water, brine and dried (Na$_2$SO$_4$). Removal of the solvent gave the title compound as a white solid (67 g, 74%). $^1$H NMR (250 MHz, CD$_3$OD)δ 4.45 (m, 2H), 2.49 (s, 1H), 1.38 (m, 3H).

b) Ethyl 5-amino-1-n-butyl-1H-imidazole-4-carboxylate

A solution of ethyl 2-amino-2-cyanoacetate (0.20 g, 1.56 mmol) and triethyl formate (0.30 mL, 1.72 mmol) in acetonitrile (5 mL) was refluxed for 1 h. After concentrating the residue was dissolved in a solution of acetonitrile (5 mL) and n-butylamine (0.17 mL, 1.72 mmol). The resulting mixture was stirred at reflux for 1 h. The solvents were removed under reduced pressure and the residue was partitioned between water and ethyl acetate. The organic layer was separated and washed with brine and dried (Na$_2$SO$_4$). After removing the solvent under reduced pressure, flash chromatography (1:1 ethyl acetate/hexane) of the residue gave 0.12 g, 40% of the title compound as an oil: $^1$H NMR (250 MHz, CDCl$_3$)δ 6.97 (s, 1H), 5.10 (s, 2H), 4.31 (q, 2H), 3.75 (t, 2H), 1.65 (m, 2H), 1.35 (m, 5H), 0.97 (t, 3H); MS(ESI) m/e 212.2 [M+H]$^+$.

c) Ethyl 5-bromo-1-n-butyl-1H-imidazole-4-carboxylate

To a solution of ethyl 5-amino-1-n-butyl-1H-imidazole-4-carboxylate (0.05 g, 0.24 mmol) in bromoform (5 mL) was added butyl nitrite (0.10 mL, 0.71 mmol). The reaction mixture was stirred at reflux for 5 h. After an aqueous work up, extracting with ethyl acetate, the combined organic extracts were washed with brine and dried (Na$_2$SO$_4$). After removing the solvent under reduced pressure, flash column chromatography (1:1 ether/hexane) of the residue gave the title compound as an oil (0.03 g, 46%). 1H NMR (250 MHz, CDCl$_3$)δ 7.50 (b, 1H), 4.41 (q, 2H), 3.95 (t, 2H), 1.70 (quintet, 2H), 1.40 (m, 5H), 1.00 (t, 3H).

d) Ethyl 5-(2-methoxymethoxy-4-methoxyphenyl)-1-n-butyl-1H-imidazole-4-carboxylate A mixture of ethyl 5-bromo-1-n-butyl-1H-imidazole-4-carboxylate (0.10 g, 0.37 mmol), 2-methoxymethoxy-4-methoxyphenylboronic acid (0.16 g, 0.73 mmol), sodium carbonate (0.08 g, 0.73 mmol) and tetrakis (triphenylphosphine)palladium(0) (0.04 g) in 12 mL of toluene/ethanol/water (10/1/1) was stirred at reflux for 24 h. After an aqueous work up, extracting with ethyl acetate (3×20 mL), the combined organic extracts were washed with brine and dried (Na$_2$SO$_4$). After removing the solvent under reduced pressure, flash column chromatography (1:1 ethyl acetate/hexane) of the residue afforded the title compound as an oil (0.06 g, 46%). $^1$H NMR (250 MHz, CDCl$_3$)δ 7.53 (s, 1H), 7.09 (d, 1H), 6.75 (d, 1H), 6.60 (dd, 1H), 5.05 (q, 2H), 4.21 (q, 2H), 3.85 (s, 3H) 3.80 (t, 2H), 3.30 (s, 3H) 1.60 (quintet, 2H), 1.30 (m, 5H), 0.80 (t, 3H).

e) 1-n-Butyl-4-hydroxymethyl-5-(2-methoxymethoxy-4-methoxyphenyl)-1H-imidazole

To a solution of ethyl 1-n-butyl-5-(2-methoxymethoxy-4-methoxyphenyl)-1H-imidazole-4-carboxylate (0.06 g, 0.17 mmol) in THF (5 mL) was added LAH (0.20 mL) at room temperature. The mixture was stirred for 2 h. After an aqueous work up, extracting with ethyl acetate (3×20 mL), the combined organic extracts were washed with brine and dried (Na$_2$SO$_4$). After removing the solvent under reduced pressure, flash column chromatography (1:1 ethyl acetate/hexane) of the residue afforded the title compound as an oil (0.05 g, 96%). $^1$H NMR (400 MHz, CDCl$_3$)δ 7.53 (s, 1H), 7.19 (d, 1H), 6.85 (d, 1H), 6.65 (dd, 1H), 5.05 (d, 2H), 4.41 (dd, 2H), 3.85 (s, 3H) 3.80 (t, 2H), 3.45 (s, 3H) 3.23 (b, 1H), 1.55 (quintet, 2H), 1.25 (quintet, 2H), 0.83 (t, 3H).

f) 1-n-Butyl-5-(2-methoxymethoxy-4-methoxyphenyl)-1H-imidazole-4-carboxaldehyde

To a solution 1-n-butyl-4-hydroxymethyl-5-(2-methoxymethoxy-4-methoxyphenyl)-1H-imidazole (0.05 g, 0.16 mmol) in toluene (5 mL) was added manganese oxide (0.04 g, 0.47 mmol). The mixture was stirred for 5 h at room temperature. The mixture was filtered and the filtrate was evaporated to dryness. Flash column chromatography (1:4 ethyl acetate/hexane) of the residue afforded the title compound as an oil (0.05 g, 94%). $^1$H NMR (250 MHz, CDCl$_3$)δ 9.65 (s, 1H), 7.58 (s, 1H), 7.13 (d, 1H), 6.80 (d, 1H), 6.65 (dd, 1H), 5.05 (s, 2H), 3.90 (s, 3H) 3.80 (t, 2H), 3.35 (s, 3H), 1.55 (quintet, 2H), 1.25 (quintet, 2H), 0.83 (t, 3H).

g) Ethyl (E)-3-[1-n-butyl-5-[2-(2-methoxymethoxy)-4-methoxyphenyl]-1H-imidazol-4-yl]-2-[(2-methoxy-4,5-methylenedioxy)phenylmethyl]-2-propenoate A solution of 1-n-butyl-5-(2-methoxymethoxy-4-methoxyphenyl)-H-imidazol-4-carboxaldehyde (0.40 g, 1.40 mmol), ethyl hydrogen 2-(2-methoxy-4,5-methylenedioxybenzyl) malonate (1.00 g, 3.50 mmol), piperidine(0.07 mL, 0.70 mmol) and acetic acid (0.04 mL, 0.70 mmol) in benzene (20 mL), equipped with a Dean-Stark apparatus, was stirred at reflux for 24 h. The solvent was removed under reduced pressure and the crude residue was dissolved in ethyl acetate and washed with 10% sodium carbonate solution, water and dried (Na$_2$SO$_4$). After removing the solvent, flash column chromatography of the residue (silica gel, 50% ethyl acetate/hexane) yielded the title compound as a brown oil (0.24 g, 33%). $^1$H NMR (250 MHz, CDCl$_3$)δ 7.63 (s, 1H), 7.35 (s, 1H), 7.13 (d, 1H), 6.70 (d, 1H), 6.65 (m, 2H), 6.51 (m, 2H), 5.75 (s, 2H), 5.05 (s, 2H), 4.07 (q, 2H), 3.87 (s, 3H) 3.77 (t, 3H), 3.35 (s, 3H), 1.55 (quintet, 2H), 1.25 (quintet, 2H), 1.10 (t, 3H), 0.83 (t, 3H).

h) Ethyl (E)-3-[1-n-butyl-5-(2-hydroxy-4-methoxy)phenyl-1H-imidazol-4-yl]-2-[(2-methoxy-4,5-methylenedioxy)phenylmethyl]-2-propenoate To a solution of the ethyl (E)-3-[1-n-butyl-5-(2-methoxymethoxy-4-methoxy-phenyl)-1H-imidazol-4-yl]-2-[(2-methoxy-4,5-methylenedioxy)phenylmethyl]-2-propenoate (0.20 g, 0.38 mmol) in ethanol (25 mL) was added a catalytic amount of concentrated HCl. After stirring at reflux for 5 h the solvent was removed under reduced pressure. The residue was dissolved in ethyl acetate and washed with sat'd. sodium bicarbonate and dried (Na$_2$SO$_4$). After removing the solvent flash chromatography of the residue (silica gel, 50% ethyl acetate/hexane) gave the title compound as a brown oil (0.18 g, 87%). $^1$H NMR (250 MHz, CDCl$_3$)δ 7.53 (s, 1H), 7.35 (s, 1H), 7.00 (d, 1H), 6.60 (d, 1H), 6.55 (m, 2H), 6.51 (m, 2H), 5.85 (s, 2H),4.39 (dd, 2H), 4.07 (q, 2H), 3.87 (s, 3H) 3.77 (t, 3H), 1.50 (quintet, 2H), 1.15 (m, 5H), 0.83 (t, 3H).

i) Ethyl (E)-3-[1-n-butyl-5-[2-(2-methoxycarbonyl)phenylmethoxy-4-methoxyphenyl]-1H-imidazol-4-yl]-2-[(2-methoxy-4,5-methylenedioxy)phenylmethyl]-2-propenoate To a solution of the ethyl (E)-3-[1-n-butyl-5-(2-hydroxy-4-methoxyphenyl)-1H-imidazol-4-yl]-2-[(2-methoxy-4,5-methylenedioxy)phenylmethyl]-2-propenoate (0.08 g, 0.16 mmol) and 2-methyl carboxylate benzylbromide (0.09 g, 0.38 mmol) in DMF (5 mL) was added sodium hydride (0.01 g, 0.47 mmol) at 0° C. The reaction stirred at room temperature for 4 h. After an aqueous work up, extracting with ethyl acetate (3×15 mL), the combined organic extracts were washed and dried (Na$_2$SO$_4$). After removing the solvent under reduced pressure, flash column chromatography (1:1 ethyl acetate/hexane) of the residue afforded the title compound as an oil (0.05 g, 46%). $^1$H NMR (250 MHz, CDCl$_3$)δ 7.98 (d, 1H), 7.60 (s, 1H), 7.48 (m, 2H), 7.35 (m, 2H), 7.15 (d, 1H), 6.65 (m, 2H), 6.50 (s, 2H), 5.83 (d, 2H), 5.45 (s, 2H),4.49 (q, 2H), 4.07 (q, 2H), 3.90 (s, 3H) 3.87 (s, 3H), 3.78 (s, 3H), 1.52 (quintet, 2H), 1.15 (m, 5H), 0.75 (t, 3H).

j) (E)-3-[1-n-Butyl-5-[2-(2-carboxyphenylmethoxy)-4-methoxyphenyl]-1H-imidazol-4-yl]-2-[(2-methoxy-4,5-methylenedioxy)phenylmethyl]-2-propenoic acid To a solution of the ethyl (E)-3-[1-n-butyl-5-[2-(2-methoxycarbonyl)phenylmethoxy-4-methoxyphenyl]-1H-imidazol-4-yl]-2-[(2-methoxy-4,5-methylenedioxy)phenylmethyl]-2-propenoate (0.04 g, 0.07 mmol) in methanol (5 mL) was added a solution of sodium hydroxide (0.01 g, 0.25 mmol) in water (2 mL). The mixture stirred at reflux for 18 h. The methanol was removed under reduced pressure and the aqueous layer was washed with ether. The aqueous layer was acidified with concentrated HCl to pH 1 and extracted with ethyl acetate (3×50 mL). The combined organic extracts were washed with water, brine and dried (Na$_2$SO$_4$). Removal of the solvent gave a white solid. Recrystallization from methanol yielded the title compound as a white solid (0.03 g, 72%): $^1$H NMR (400 MHz CD$_3$OD) δ 7.98 (d, 1H), 7.80 (s, 1H), 7.48 (s, 1H), 7.35 (m, 3H), 7.15 (d, 1H), 6.65 (m, 2H), 6.50 (s, 1H), 6.38 (s, 1H), 5.78 (s, 2H), 5.55 (dd, 2H), 4.10 (s, 2H), 3.85 (s, 3H) 3.65 (s, 3H), 1.50 (quintet, 2H), 1.11 (quintet, 2H), 0.70 (t, 3H); MS(ESI) m/e 615.2 [M+H]$^+$; mp: 178° C. (methanol); Anal. (C$_{34}$H$_{34}$N$_2$O$_9$) calcd: C, 66.37; H, 5.58; N, 4.56. found: C, 66.10; H, 5.32; N, 4.19.

EXAMPLE 3

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of Formula (I):

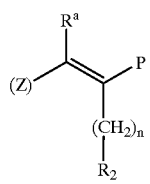

(I)

wherein Z is (d)

[structure: phenyl substituted with $R_4$, $R_3$, $R_5$ attached to a 5-membered ring with methyl group, containing D, N and $R_1$]

(e)

[structure: phenyl substituted with $R_4$, $R_3$, $R_5$ attached to a 5-membered ring with methyl group, containing N, D and $R_1$]

or (f)

[structure: phenyl substituted with $R_4$, $R_3$, $R_5$ attached to a 5-membered ring containing N and D]

D is O or S;

P is tetrazol-5-yl, $CO_2R_6$ or $C(O)N(R_6)S(O)_qR_{10}$;

$R^a$ is independently hydrogen or $C_{1-6}$ alkyl;

$R_1$ is independently hydrogen, Ar, $C_{1-6}$ alkyl, or $C_{1-6}$ alkoxy;

$R_2$ is Ar, $C_{1-8}$ alkyl, $C(O)R_{14}$ or (c)

[structure: cyclic $(CH_2)_m$ with $R_3$, $R_4$, $R_5$ substituents]

$R_3$ and $R_5$ are independently $R_{13}OH$, $C_{1-8}$ alkoxy, $S(O)_qR_{11}$, $N(R_6)_2$, $NO_2$, Br, F, I, Cl, $CF_3$, $NHCOR_6$, $R_{13}CO_2R_7$, —X—$R_9$—Y, —X(C($R_6$)$_2$)$OR_6$, —$(CH_2)_m$X'$R_8$ or —X$(CH_2)_nR_8$ wherein each methylene group within —X$(CH_2)_nR_8$ may be unsubstituted or substituted by one or two —$(CH_2)_n$Ar groups;

$R_4$ is independently $R_{11}$, OH, $C_{1-5}$ alkoxy, $S(O)_qR_{11}$, $N(R_6)_2$, Br, F, I, Cl or $NHCOR_6$, wherein the $C_{1-5}$ alkoxy may be unsubstituted or substituted by OH, methoxy or halogen;

$R_6$ is independently hydrogen or $C_{1-8}$ alkyl, $R_7$ is independently hydrogen, $C_{1-10}$ alkyl, $C_{2-10}$ alkenyl or $C_{2-8}$ alkynyl, all of which may be unsubstituted or substituted by one or more OH, $N(R_6)_2$, $CO_2R_{12}$, halogen or $XC_{1-10}$ alkyl; or $R_7$ is $(CH_2)_n$Ar;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N(R_6)_2$, $C(R_{11})_2N(R_7)_2$, $C(O)N(R_6)_2$, $NR_7C(O)NR_7SO_2R_{11}$, $OR_6$, or tetrazole which is substituted or unsubstituted by $C_{1-6}$ alkyl;

$R_9$ is independently a bond, $C_{1-10}$ alkylene, $C_{1-10}$ alkenylene, $C_{1-10}$ alkylidene, $C_{1-10}$ alkynylene, all of which may be linear or branched, or phenylene, all of which may be unsubstituted or substituted by one of more OH, $N(R_6)_2$, COOH or halogen;

$R_{10}$ is independently $C_{1-10}$ alkyl, $N(R_6)_2$ or Ar;

$R_{11}$ is independently hydrogen, Ar, $C_{1-8}$ alkyl, $C_{2-8}$ alkenyl, $C_{2-8}$ alkynyl, all of which may be unsubstituted or substituted by one or more OH, $CH_2OH$, $N(R_6)_2$ or halogen;

$R_{12}$ is independently hydrogen. $C_{1-6}$ alkyl, $C_{2-6}$ alkenyl or $C_{2-7}$ alkynyl;

$R_{13}$ is independently divalent Ar, $C_{1-10}$ alkylene, $C_{1-10}$ alkylidene, $C_{2-10}$ alkenylene, all of which may be unsubstituted or substituted by one or more OH, $CH_2OH$, $N(R_6)_2$ or halogen;

$R_{14}$ is independently hydrogen, $C_{1-10}$ alkyl, $XC_{1-10}$ alkyl, Ar or XAr:

$R_{15}$ is independently hydrogen, Ar, $C_{1-6}$ alkyl, or XAr;

$R_{1-6}$ is independently $C_{1-6}$ alkyl or phenyl substituted by one or more $C_{1-6}$ alkyl, OH, $C_{1-5}$ alkoxy, $S(O)_qR_6$, $N(R_6)_2$, Br, F, I, Cl, $CF_3$ or $NHCOR_6$;

X is independently $(CH_2)_n$, O, $NR_6$ or $S(O)_q$;

X' is independently O, $NR_6$ or $S(O)_q$;

Y is independently $CH_3$ or $X(CH_2)_n$Ar;

Ar is:

(a)

[structure: phenyl]

(b)

[structure: bicyclic with A and B atoms]

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-10}$ alkyl, $(CH_2)_qCO_2R_6$, $C(O)N(R_6)_2$, CN, $(CH_2)_n$OH, $NO_2$, F, Cl, Br, I, $N(R_6)_2$, $NHC(O)R_6$, $O(CH_2)_mC(O)_nR_aSO_2R_{16}$, $(CH_2)_mOC(O)NR_aSO_2R_{16}$, $O(CH_2)_mNR_aC(O)NR_aSO_2R_{16}$ or tetrazolyl which may be substituted or unsubstituted by one or two $C_{1-6}$ alkyl, $CF_3$ or $C(O)R_6$;

m is independently 1 to 3;

n is independently 0 to 6;

q is independently 0, 1 or 2;

provided $R_3$, $R_4$ and $R_5$ are not O—O(CH$_2$)$_n$Ar or O—OR$_6$;

or a pharmaceutically acceptable salt thereof.

2. A compound of claim 1 wherein P is CO$_2$R$_6$; R$_1$ is hydrogen; R$_2$ is Ar, cyclohexyl or C$_{1-4}$ alkyl; R$_3$ and R$_5$ are independently hydrogen, CO$_2$R$_6$, OH, C$_{1-8}$ alkoxy, C$_{1-8}$ alkyl, N(R$_6$)$_2$, NO$_2$, Br, F, Cl, I, R$_{13}$CO$_2$R$_7$, X(CH$_2$)$_n$R$_8$, (CH$_2$)$_m$X'R$_8$, or X(C(R$_6$)$_2$)$_m$OR$_6$; R$_4$ is hydrogen, OH, C$_{1-5}$ alkoxy, N(R$_6$)$_2$, Br, F, Cl, I, NHCOCH$_3$, or S(O)$_q$C$_{1-5}$ alkyl wherein the C$_{1-5}$ alkyl may be unsubstituted or substituted by OH, methoxy or halogen; R$_6$ is hydrogen, methyl or ethyl; R$_7$ is hydrogen, C$_{1-10}$ alkyl, C$_{2-10}$ alkenyl or C$_{2-8}$ alkynyl, all of which may be unsubstituted or substituted by one or more OH, N(R$_6$)$_2$, CO$_2$R$_{12}$, halogen, or R$_7$ is (CH$_2$)$_n$Ar wherein n is zero or 1 and Ar is substituted phenyl; R$_{11}$ is hydrogen, phenyl, pyridyl all of which may be substituted or unsubstituted by one or two C$_{1-4}$ alkyl groups; C$_{1-8}$ alkyl, C$_{2-8}$ alkenyl, C$_{2-8}$ alkynyl, all of which may be substituted or unsubstituted by one or more OH, CH$_2$OH, N(R$_6$)$_2$, or halogen; R$_{12}$ is hydrogen or C$_{1-6}$ alkyl; R$_{13}$ is phenyl, pyridyl, or C$_{2-10}$ alkylene, all of which may be unsubstituted or substituted by one or more CO$_2$R$_6$, OH, CH$_2$OH, N(R$_6$)$_2$, or halogen; and R$_{15}$ is hydrogen or C$_{1-6}$ alkyl.

3. A compound of claim 2 wherein P is CO$_2$H; R$_1$ is hydrogen; R$_2$ is a group Ar wherein Ar is a group (a) or (b) and in said group (a) or (b), Z$_1$ and Z$_2$ are independently hydrogen, CO$_2$R$_6$, (CH$_2$)$_n$OH, C$_{1-4}$ alkyl or C$_{1-6}$ alkoxy and A is CH$_2$, and one or both Bs are O; R$_3$ is Br, Cl, C$_{1-8}$ alkoxy or X(CH$_2$)$_n$R$_8$, wherein X is O, n is 0, 1, or 2, and R$_8$ is selected from: CO$_2$H, OH, tetrazolyl optionally substituted by C$_{1-8}$ alkyl; CONR$_7$SO$_2$R$_{11}$ wherein R$_7$ is H or C$_{1-8}$ alkyl, R$_{11}$ is C$_{1-8}$ alkyl or phenyl optionally substituted by Br, Cl, F, C$_{1-8}$ alkyl; or R$_8$ is phenyl or pyridyl substituted by one or more Br, Cl, CO$_2$H, CH$_2$OH; R$_5$ is methoxy or N(R$_6$)$_2$ wherein R$_6$ is H or methyl; R$_4$ is hydrogen; R$_6$ is hydrogen, methyl or ethyl; R$_7$ is hydrogen, C$_{1-10}$ alkyl, C$_{2-10}$ alkenyl or C$_{2-8}$ alkynyl, all of which may be unsubstituted or substituted by one or more OH, N(R$_6$)$_2$, CO$_2$R$_{12}$, halogen, or R$_7$ is (CH$_2$)$_n$Ar wherein R$_7$ is (CH$_2$)$_n$Ar and n is preferably zero or 1 and Ar is preferably phenyl substituted or unsubstituted by halogen or C$_{1-5}$ alkoxy; R$_{11}$ is hydrogen, phenyl, pyridyl wherein the phenyl or pyridyl be substituted or unsubstituted by one or two C$_{1-4}$ alkyl groups; C$_{1-8}$ alkyl, C$_{2-8}$ alkenyl, C$_{2-8}$ alkynyl, all of which may be substituted or unsubstituted by one or more OH, CH$_2$OH, N(R$_6$)$_2$, or halogen; R$_{12}$ is hydrogen or C$_{1-6}$ alkyl; R$_{13}$ is phenyl, pyridyl, or C$_{2-10}$ alkylene, all of which may be unsubstituted or substituted by one or more CO$_2$R$_6$, OH, CH$_2$OH, N(R$_6$)$_2$, or halogen; and R$_{15}$ is hydrogen, ethyl, isopropyl, n-butyl, cyclopropylmethyl or cyclopropylethyl.

4. A compound of claim 1 selected from:

(E)-alpha-[[5-[2-[(2-carboxyphenyl)methoxy]-4-methoxyphenyl]isoxazol-4-yl]methylene]-6-methoxy-1,3-benzodioxole-5-propanoic acid;

(E)-alpha-[[3-[2-[(2-carboxyphenyl)methoxy]-4-methoxyphenyl]isoxazol-4-yl]methylene]-6-methoxy-1,3-benzodioxole-5-propanoic acid; and (E)-alpha-[[3-Butyl-4-[2-[(2-carboxyphenyl)methoxy]-4-methoxyphenyl]isoxazol-5-yl]methylene]-6-methoxy-1,3-benzodioxole-5-propanoic acid.

5. A pharmaceutical composition comprising a compound of claim 1 and a pharmaceutically acceptable carrier.

6. A method of treatment of diseases caused by an excess of endothelin comprising administering to a subject in need thereof, an effective amount of an endothelin receptor antagonist of claim 1.

7. A method of treating renal failure or cerebrovascular disease which comprises administering to a subject in need thereof, an effective amount of a compound of claim 1.

8. A method for the prophylaxis and treatment of radio-contrast induced renal failure which comprises administering to a subject in need thereof, an effective amount of a compound of claim 1.

9. A method of treatment of congestive heart failure which comprises administering to a subject in need thereof, an effective amount of a compound of claim 1.

10. A method of treatment of unstable angina, coronary vasospasm and myocardial salvage which comprises administering to a subject in need thereof, an effective amount of a compound of claim 1.

11. A method of preventing or treating restenosis which comprises administering to a subject in need thereof, an effective amount of a compound of claim 1.

12. A method of treatment of pulmonary hypertension which comprises administering to a subject in need thereof, an effective amount of a compound of claim 1.

13. A method of treatment of stroke or subarachnoid hemorrhage which comprises administering to a subject in need thereof, an effective amount of a compound of claim 1.

* * * * *